United States Patent
Polovsky et al.

(10) Patent No.: US 6,573,375 B2
(45) Date of Patent: Jun. 3, 2003

(54) LIQUID THICKENER FOR SURFACTANT SYSTEMS

(75) Inventors: Stuart Barry Polovsky, Matawan, NJ (US); Carmella A. Barbeito, Edison, NJ (US); Wing Kin Li, New Brunswick, NJ (US); Edward F. Diantonio, Staten Island, NY (US); Russell Lowell Kreeger, Flemington, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 120 days.

(21) Appl. No.: 09/741,514

(22) Filed: Dec. 20, 2000

(65) Prior Publication Data

US 2002/0123625 A1 Sep. 5, 2002

(51) Int. Cl.⁷ .................................................. C07H 1/00
(52) U.S. Cl. .............................. 536/123.1; 536/123.12; 536/123.13
(58) Field of Search ........................ 536/123.1, 123.12, 536/123.13

(56) References Cited

U.S. PATENT DOCUMENTS

| | | | |
|---|---|---|---|
| 3,640,998 A | 2/1972 | Mansfield et al. .......... 260/210 |
| 3,655,645 A | 4/1972 | Jacques ...................... 260/234 |
| 3,737,426 A | 6/1973 | Throckmorton et al. .... 260/210 |
| 4,011,389 A | 3/1977 | Langdon ........................ 536/4 |
| 4,137,401 A | 1/1979 | Lemieux et al. ............ 536/116 |
| 4,147,652 A | 4/1979 | Kaniecki .................... 252/156 |
| 4,268,498 A | 5/1981 | Gedeon et al. ............... 424/59 |
| 4,324,703 A | 4/1982 | Seldner ....................... 252/522 |
| 4,364,930 A | 12/1982 | Griat et al. .................... 424/81 |
| 4,450,090 A | 5/1984 | Kinney ....................... 252/106 |
| 4,528,106 A | 7/1985 | Grolitzer ................... 252/8.55 |
| 4,627,931 A | 12/1986 | Malik ......................... 252/153 |
| 4,687,843 A | 8/1987 | Smolin et al. ............. 536/18.3 |
| 4,803,010 A | * 2/1989 | Ogino et al. ................ 510/422 |
| 4,834,903 A | 5/1989 | Roth et al. ............. 252/174.17 |
| 5,059,443 A | * 10/1991 | Ennis et al. ................ 426/531 |
| 5,109,127 A | 4/1992 | Sekiguchi et al. .......... 536/115 |
| 5,190,747 A | 3/1993 | Sekiguchi et al. ............ 424/56 |
| 5,192,462 A | * 3/1993 | Gloor et al. .................. 424/59 |
| 5,230,835 A | 7/1993 | Deguchi et al. ............. 252/550 |
| 5,246,695 A | 9/1993 | Hintz et al. ................... 424/70 |
| 5,270,461 A | 12/1993 | Walele et al. ............... 536/116 |
| 5,298,637 A | * 3/1994 | Cooper ....................... 554/157 |
| 5,384,334 A | 1/1995 | Polovsky et al. ........... 514/777 |
| 5,393,454 A | 2/1995 | Mondin et al. ........ 252/174.23 |
| 5,501,813 A | 3/1996 | Fischer et al. ......... 252/174.17 |
| 5,502,175 A | 3/1996 | Desai et al. ................ 536/18.3 |
| 5,597,406 A | 1/1997 | Fischer et al. .............. 106/237 |
| 5,756,716 A | 5/1998 | Farone et al. ............... 536/120 |
| 5,780,416 A | 7/1998 | Kiewert et al. ............. 510/422 |
| 5,814,341 A | 9/1998 | Fankhauser et al. ........ 424/493 |
| 5,849,679 A | 12/1998 | Toda et al. ................. 510/119 |
| 5,869,679 A | 2/1999 | Verhoff et al. .............. 548/188 |
| 5,872,245 A | 2/1999 | Wilson ........................ 536/119 |
| 5,939,081 A | 8/1999 | Ansmann et al. ........... 424/401 |
| 5,945,519 A | 8/1999 | Desai et al. ................ 536/18.6 |

FOREIGN PATENT DOCUMENTS

| | | |
|---|---|---|
| EP | 621283 | 4/1994 |
| JP | 97634 | 4/1993 |

OTHER PUBLICATIONS

Glucamate®DOE–120 "A New Agent for Viscosity Enhancement", Stuart B. Polovsky, Ph. D. et al., 1999.
XIV Jornadas Del Comite Espanol De La Detergencia Tensioactivos Y Afines, PEG_120 Methyl Glucoside Dioleate, Polovsky et al. pp 83–102, 1999.
The Journal of the American Oil Chemists Society, "The Preparation and Properties of Polyoxyethylene Methyl Glucoside Fatty Esters" Otey et al. Oct. 1961.

* cited by examiner

Primary Examiner—Dwayne C. Jones

(57) ABSTRACT

Compositions comprising alkoxylated lipophilic polyol compounds, e.g., ethoxylated, esterified methyl glucosides, are disclosed wherein at least 5% of the polyol derivatives have about three moles of the lipophilic substituent per mole of polyol. Quite advantageously, the disclosed polyol derivatives can be dissolved into aqueous solutions to provide liquid thickeners suitable for thickening surfactant-containing compositions, e.g., shampoos, at cold processing temperatures.

12 Claims, No Drawings

LIQUID THICKENER FOR SURFACTANT SYSTEMS

FIELD OF THE INVENTION

The present invention relates to alkoxylated, lipophilic polyol compounds having about three moles of lipophilic substitutuents per mole of polyol and, more specifically, to the use of such compounds as thickeners in liquid surfactant compositions.

BACKGROUND OF THE INVENTION

Liquid compositions containing surfactants, e.g., shampoos, dishwashing liquids and other personal care and industrial products, typically contain thickeners in order to viscosity the liquid compositions sufficiently to enable convenient handling. Often, the thickeners comprise an alkoxylated polyol containing lipophilic substituents, e.g., ethoxylated methyl glucose esterified with a fatty acid. Such thickeners are typically alkoxylated to an extent sufficient to provide water-solubility and provide viscosification to the liquid surfactant composition. The lipophilic substituent, e.g., fatty acid, typically provides associative thickening characteristics to the thickener.

Often, the thickeners are introduced to the liquid surfactant compositions in solid form and mixed under conditions effective to dissolve the thickener into the liquid surfactant composition and cause significant viscosity increases, e.g., up to about 2,000 to 100,000 centipoise ("cP") or higher. Frequently, the mixing must be conducted at elevated temperatures, e.g., from about 50 to 80° C., in order to promote the dissolution of the thickener and obtain the desired viscosity enhancement (known in the art as "hot processing"). However, formulators of products comprising thickened, surfactant-containing liquids, e.g., shampoos, desire the ability to formulate their products at ambient temperatures, e.g., from about 20 to 30° C. (known in the art as "cold processing"). Additionally, formulators also desire thickeners which can be introduced to the liquid surfactant compositions in a liquid form rather than a solid form. The ability to introduce the thickener in a liquid form can provide a formulator with a greater degree of accuracy in introducing the correct amount of thickener to the liquid surfactant system and also better facilitate automated processing.

Accordingly, improved compositions suitable for use as thickeners in liquid surfactant systems are desired. Preferably, the thickeners can be introduced by cold processing and in a liquid state. Methods for using the compositions to thicken liquid compositions comprising surfactants are also desired.

SUMMARY OF THE INVENTION

By the present invention, alkoxylated, lipophilic polyol compounds, e.g., ethoxylated, esterified methyl glucosides, are provided which are useful, for example, as thickeners in liquid surfactant-containing systems. In the compositions of the present invention, at least 5 wt. % of the polyol compounds have about three moles of the lipophilic substituent per mole of polyol. Quite surprisingly, it has been found in accordance with the present invention that the presence of a sufficient portion of the polyol compounds having about three moles of the lipophilic substituent per mole of the polyol can enhance the ability of the composition to thicken a liquid surfactant system, preferably at cold processing temperatures.

In addition, the present invention provides processes for preparing the compositions which include the steps of alkoxylating the polyol with a suitable alkoxylation reagent, e.g., ethylene oxide, and introducing a lipophilic substituent, e.g., by esterification with a fatty acid. The processes also provide for introducing the lipophilic substituents prior to the alkoxylation step as well as sequential introductions of the lipophilic substituent and the alkoxylating reagent.

DETAILED DESCRIPTION OF THE INVENTION

The polyols suitable for use as starting materials in accordance with the present invention comprise any compounds having three or more hydroxyl groups per molecule which are reactive with the alkoxylation reagents and the lipophilic reagents described below. General examples include glycerols, polyglycerols, sugar alcohols, e.g., sorbitol or sorbitan, and saccharides, e.g., glucose and its derivatives. More specific examples of the polyols which can be used according to the invention include, but are not limited to, trimethylolethane [2-methyl-2-(hydroxymethyl)-1,3-propanediol], trimethylolpropane[2-ethyl-2-(hydroxymethyl)-1,3-propanediol], pentaerythritol (2,2-dimethylol-1,3-propanediol), diglycerol (glycerol dimer), dipentaerythritol, glycerol, and the like.

Preferred polyol starting materials for use in accordance with the present invention are glucose derivatives, more preferably, glycosides, e.g., glucosides, galactosides, monosaccharides, oligosaccharides having up to about 10 saccharide repeat units per molecule and sucrose. Especially preferred glucosides include alkyl glucosides, such as for example, methyl glucoside, ethyl glucoside, propyl glucoside, butyl glucoside and amyl glucoside.

Such polyols are commercially available.

Suitable reagents for alkoxylating the polyols are alkylene oxides, such as, for example, ethylene oxide, propylene oxide, butylene oxide and mixtures thereof. Other alkoxylating reagents, e.g., higher alkylene oxides, may be used in accordance with the present invention. Alkylene oxides suitable for use in accordance with the present invention are commercially available. The amount of alkoxylation in accordance with the present invention is that which is effective to provide water solubility and viscosification in a liquid surfactant composition. Typically, such amounts range from about 50 to 400, preferably from about 80 to 180 and more preferably from about 100 to 160 moles of alkylene oxide per mole of polyol. Methods for alkoxylating polyols, e.g. by direct alkoxylation, are known to those skilled in the art. Alternatively, partially alkoxylated methyl glucosides, e.g., GLUCAM™ E-20 (PEG-20 methyl glucoside) available from Amerchol Corporation, Edison, N.J., can be used as a starting material which can then be further alkoxylated to contain the desired degree of alkoxylation.

The lipophilic reagents suitable to derivatize the polyols of the present invention include any compounds which are reactive with the polyols and have sufficient molecular weight to promote associative thickening when introduced into a liquid, surfactant-containing system. Typically, the lipophilic reagents comprise hydrocarbon or substituted hydrocarbon moieties with from about 8 to 30, preferably from about 12 to 26 and more preferably from about 16 to 22 carbon atoms per molecule. The particular structure of the lipophilic reagents is not critical to the present invention and may, for example, be alkyl, aryl, alkylaryl, alkenyl and may be cyclic, branched or straight. Typically, the reagents are fatty acids, fatty esters, epoxides, halides glycidyl ethers, or vegetable or animal oils. The reagents typically provide either an ester or ether linkage to the polyol. Stated another way, in the case of a glucose derivative, for example, the ether or ester is typically attached to the glucose derivative indirectly through a polyoxyalkylene chain.

Examples of suitable fatty acids include natural or synthetic saturated or unsaturated acids which are linear or branched. The fatty acids can be used alone or as a mixture. Natural fatty acids include, for example, saturated or unsaturated linear fatty acids such as caproic acid, enanthic acid, caprylic acid, pelargonic acid, decanoic acid, lauric acid, myristic acid, palmitic acid, stearic acid, linolic acid, oleic acid, capric acid and undecanoic acid which are typically obtained by hydrolyzing vegetable oils and animal oils such as coconuts oils, palm oil, tallow, linseed oil and soybean oil. Examples of synthetic fatty acids, include linear or branched fatty acids prepared by oxidizing olefin polymers. It is also possible to use fatty acids derived from microorganisms such as, for example, γ-linolenic acid. Further, as the lower alkyl ester of the fatty acid, alkyl esters having 1 to 8 carbon atoms such as methyl, ethyl or propyl ester of the fatty acid described above can be used. The fatty acid esters of hexose or the alkyl glycoside thereof can be synthesized by using various known methods, including ester synthesis using lipase and the like: for example; (1) an ester exchange reaction between starting oils or fats and a hexose or its alkylglycoside, (2) an ester exchange reaction between a lower alkyl ester of a fatty acid and a hexose or its alkyl glycoside, or (3) an ester synthesis between a fatty acid and a hexose or its alkyl glycoside. In addition, a synthesis process using a fatty acid chloride and a hexose or its alkyl glycoside may also be employed.

Examples of other suitable lipophilic reagents include glycidyl ethers, e.g., nonylphenylglycidyl ether or dodecylphenyl glycidyl ether, alpha-olefin epoxides, e.g., 1,2-epoxyhexadecane and their respective chlorohydrins, or alkyl halides, e.g., dodecylbromide, and the above-mentioned vegetable and animal oils. Halogenated products of fatty acids can also be used as the lipophilic reagent.

The amount of the lipophilic reagent used to derivatize the polyols of the present invention is preferably effective to promote associative thickening behavior of the polyol derivatives when present in a liquid surfactant composition. Typically, the average substitution level of the lipophilic substituent is about 3, e.g., from 2.5 to 4, preferably from about 2.5 to 3.9 and more preferably from about 2.8 to 3.6, moles per mole of polyol. Details concerning the derivatization of polyols to comprise lipophilic substituents are known to those skilled in the art. The average amount of lipophilic substituent per mole of polyol (referred to in the art as Degree of Substitution "DS") can be determined by any technique known to those skilled in the art, e.g., by nuclear magnetic resonance spectroscopy ("NMR"). The lipophilic reagents suitable for use in accordance with the present invention are commercially available.

In accordance with the present invention, the alkoxylated, lipophilic polyol compounds comprise a mixture of compounds substituted with varying amounts of the lipophilic substituent depending upon the available hydroxyl groups on the polyol starting material. At least 5% of the polyol compounds in the composition have about three moles of the lipophilic substituent per mole of polyol. For example, in the case of an ethoxylated, esterified methyl glucoside, at least 5% of the compounds are substituted with about three moles of the lipophilic substituent per mole of the methyl glucoside. Typically, at least 25%, preferably at least 50% and more preferably at least 75% of the polyol derivatives in the composition have about three moles of the lipophilic substituent per mole of polyol. Typically, the balance of the composition comprises polyol derivatives having one, two or four moles of the lipophilic substituent per mole of polyol. Typically, less than about 75%, preferably less than about 50% and more preferably less than about 25% of the polyols in the composition comprise one, two or four moles of the lipophilic substituent per mole of polyol.

The sequence in which the alkylene oxide and lipophilic substituents are reacted onto the polyol is not critical to the present invention. In one aspect of the invention, the alkoxylation reaction is conducted first, followed by substitution of the lipophilic substituent onto the polyol. In another aspect of the invention, the polyol is first substituted with the lipophilic substituent followed by alkoxylation. In still yet another aspect of the invention, the polyol is partially esterified, e.g., to comprise one or two moles (on average) of the lipophilic substituent per mole of polyol, then ethoxylated, then subsequently esterified, e.g., to comprise about three moles of the lipophilic substituent per mole of polyol. Alternatively, the polyol can be partially ethoxylated, esterified and then ethoxylated again to the desired level. Moreover, the starting material can be the polyol, a partially alkoxylated polyol or a polyol that is partially reacted with the lipophilic reagent, or both.

The derivatizations are typically conducted under subatmospheric pressure, e.g., from about 0.001 to 1.0 atmospheres, and at a temperature in the range of about 110 to 180° C. for the alkoxylation step and about 120 to 200° C. for the lipophilic substitution step. Catalysts may or may not be used for the derivatizations. Typically, however, catalysts are employed to enhance the reaction rate. The catalysts can be acidic, basic, or neutral. Preferred catalysts for the alkoxylation step include Na, NaOCH$_3$, KOH, NaOH, K$_2$CO$_3$, Na$_2$CO$_3$. Preferred catalysts for the lipophilic substitution step include Na$_2$CO$_3$, KOH, NaOH, acids including p-toluenesulfonic acid ("p-TSA"), H$_2$SO$_4$, HCl, and others including organic titanates, e.g., tetraisopropyl titanate available as Tyzor™ catalyst from DuPont Company, Wilmington, Del. Further details concerning the manufacture of alkoxylated, lipophilic polyol compounds are known to those skilled in the art and are described, for example, in U.S. Pat. Nos. 4,687,843, 5,109,127, 5,501,813 and 5,502,175.

The product produced from the derivatization reactions is typically in the form of a solid in a granulated or powdered form. The solid product is suitable for packaging and shipment to customers.

In a preferred aspect of the invention, the alkoxylated, lipophilic polyol derivatives are dissolved in a suitable solvent to provide a liquid thickener suitable for use in viscosifying surfactant-containing liquid compositions. Any suitable liquids capable of dissolving the polyol derivatives are suitable for use in accordance with the present invention. Preferably, the liquids are aqueous with or without additional water miscible liquids. For example, suitable solvents include alkylene glycols having about 2 to 5 carbon atoms per molecule, such as propylene glycol, ethylene glycol, butylene glycol, propane diol and butane diol. Other solvents, such as for example, polyalkylene glycols, e.g., CARBOWAX™ PEG and UCON™ Fluids available from Union Carbide Corporation, Danbury, Conn., may also be employed. When the product is provided in a liquid form, it typically comprises from about 20 to 60 preferably from about 30 to 50 of the polyol derivative with the balance comprising the liquid solvent and any desired additives, such as, for example, preservatives, biocides, etc., which are generally present in minor amounts, e.g. less than about 5 wt % based on the total weight of the liquid composition. In addition, when in liquid form it is preferred that the liquid containing the thickener has a viscosity which is low enough to permit the liquid to be pumped or poured without difficulty. Typically, the viscosity is less than about 6,000 cP, preferably less than about 4,000 cP. As used herein, the term viscosity means the viscosity measured with a Brookfield Viscometer with a suitable spindle and rotational speed as determined by one skilled in the art, e.g., spindle 6 to 10 rpm.

In one preferred aspect of the invention when the polyol is a glucose derivative, the liquid composition comprises from about 10 to 30 wt % water, from about 30 to 50 wt % propylene glycol and from about 30 to 50 wt % of the glucose derivative. An especially preferred composition comprises about 20 wt % water, about 40 wt % propylene glycol and about 40 wt % of the glucose derivative.

The alkoxylated, lipophilic polyol derivatives of the present invention have a variety of end used applications, such as, for example, personal care applications and industrial applications. Typical personal care applications include, for example, pharmaceutical and cosmetic compositions, such as, for example, shampoos, conditioners, ointments, skin creams, lotions, soaps, and the like. Typical industrial applications include, for example, use as viscosity adjusters for general fluids handling and for surfactant applications, such as, dishwashing liquids, laundry detergents, suspension aids, as adhesion promoters and coating materials.

In one aspect of the invention, the alkoxylated lipophilic polyol derivatives are used for thickening liquid compositions comprising one or more surfactants. Illustrative surfactants may include: anionics including fatty acid soaps, alkyl sulfates, alkyl ether sulfates, alkyl or aryl sulfonates, sulfosuccinatos, sarcosinatos, alkyl glucose esters or their alkoxylates and in particular sodium lauryl sulfate, ammonium lauryl sulfate, triethanolamine lauryl sulfate, sodium laureth sulfate, alpha olefin sulfonate, disodium laureth sulfosuccinates, triethanolamine stearate; nonionics including methyl glucose esters or their alkoxylates, fatty acid alkanol amides, polyglycol ethers or their alkyl or aryl derivatives, hydroxylated lanolin, lanolin alcohols and in particular oleth-20, ceteareth-20, methyl glucose dioleate, methyl glucose stearate, glycerol monostearate, cocoyl diethanolamide, nonoxynal-7 and octoxynol-8; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl β-aminopropionates, betaines, alkyl imidazolines and in particular cocoamphocarboxy glycinate, cocamidopropyl betaine and caproamphocarboxy propionate.

In this aspect of the invention, a first liquid comprising the alkoxylated, lipophilic polyol compounds, is combined with a second liquid comprising a surfactant under mixing conditions, in order to provide a viscosity enhancement of at least 10%, preferably at least 50%, more preferably at least 100% and most preferably at least 200%. As used herein, the term "Viscosity Enhancement" means the enhancement in viscosity, expressed as a percentage, in a surfactant-containing liquid composition between alkoxylated, lipophilic polyol compounds of the present invention compared to alkoxylated, lipophilic polyol compounds wherein a substantial fraction, e.g., at least 90%, of the compounds have about two moles, i.e., 1.5 to 2.5 moles, of lipophilic substituent per mole of polyol. For the measurement of Viscosity Enhancement, the mixing of the surfactant system is conducted at a temperature sufficient to dissolve the components, e.g., from ambient to about 80° C., with adequate mixing (preferably with no foaming) for about 2 to 3 hours. For determining Viscosity Enhancement, the alkoxylated, lipophilic polyol is utilized in the liquid surfactant composition at an active concentration of from about 0.1 to 5 wt %, preferably from about 0.1 to 1 wt %, based on the total weight of the liquid surfactant composition. For comparison purposes, the active concentration should be essentially the same. For this measurement a Brookfield RVT viscometer with a No. 6 spindle at 10 rpm is generally suitable. The viscosity measurement should be taken at a fixed temperature, e.g., 22.5° C. Also, the comparison should be made using polyol derivatives having similar alkylene oxide substitution levels, e.g., within ±30 alkylene oxide units, and a similar lipophilic substituent, e.g., within ±2 carbon atoms per molecule.

A preferred surfactant composition for determining the Viscosity Enhancement comprises the following ingredients combined as described below.

| Ingredients | wt % |
| --- | --- |
| Deionized Water | QS to 100 |
| Sodium Laureth Sulfate −2 (26 wt % active) | 40.00 |
| Cocamidopropyl Betaine (35 wt % active) | 11.50 |
| DMDM Hydantoin | 0.4 |
| Thickener (40 wt % polyol compound, 40 wt % propylene glycol, 20 wt % water) | 1.25 |

Procedure: Add Sodium Laureth Sulfate—2 and Cocamidopropyl Betaine to the water in order, one at a time, until completely uniform before adding the next ingredient. Once uniform add the thickener with stirring and heat to 70° C. Once the thickener is totally dissolved start cooling system to 40° C. At 40° C. add DMDM Hydantoin and continue to cool to room temperature. Record viscosity after 24 hours.

Quite advantageously, it has been found in accordance with the present invention that personal care products, e.g., shampoos, skin creams and the like, may provide the following desirable characteristics. In the case of shampoos and other hair care products; improved rinseability, feel, lathering, combing potential, synergy with other ingredients, clarity and salt tolerance may be obtained. In the case of skin care products; improved anti-irritation properties, fatting agents, moisturization and dermatological compatibility may be obtained.

A typical cleansing formulation for skin or hair comprising the alkoxylated, lipophilic polyol compounds of the present invention may contain the following ingredients and can be prepared as described below.

| Ingredients | wt % |
| --- | --- |
| Deionized Water | QS |
| Polyquaternium-10 | 0.20 |
| Sodium Laureth Sulfate (26 wt % active) | 40.00 |
| Cocamidopropyl Betaine (35 wt % active) | 11.50 |
| Disodium Laureth Sulfosuccinate | 5.00 |

-continued

| Ingredients | wt % |
|---|---|
| (40 wt % active) | |
| Thickener (40 wt % polyol compound, 40 wt % propylene glycol, 20 wt % water) | 0.50 |
| DMDM Hydantoin | 0.40 |

Procedure: Add Polyquaternium-10 to room temperature deionized water with adequate agitation. When uniform heat to 70° C. and mix until fully hydrated. Once fully hydrated add the remaining ingredients up until DMDM Hydantoin, one at a time in order, waiting until for each to be dissolved before adding the next. Allow to cool to 40° C. At 40° C. add DMDM Hydantoin. Continue to cool to room temperature.

EXAMPLES

The following examples are provided for illustrative purposes and are not intended to limit the scope of the claims which follow. In the examples, the amounts recited are given in weight percent unless otherwise indicated.

Example 1 (Comparative)

Preparation of PEG-120 Methyl Glucose Dioleate-PG-Water Blend

A sample of PEG-120 Methyl Glucose Dioleate (available from Amerchol Corporation, Edison, N.J., under the tradename Glucamate™ DOE-120) of 1000 grams ("gm") was placed in a flask equipped for agitation and heating. To this was added 1000 gm of propylene glycol and 500 gm of water. The mixture was heated to 60° C. with stirring. Upon melting and continued agitation, the solids dissolved and the solution become fluid and transparent.

The final liquid product was then allowed to cool to room temperature. The product had a viscosity of <2000 cP at room temperature.

Example 2

Preparation of PEG-100 Methyl Glucoside Trioleate-PG-Water Blend

Into a one liter pressure reactor, 192 gm of PEG-20 methyl glucoside (Glucam™ E-20, available from Amerchol Corporation, Edison, N.J.) was poured. To this was added 1 gm of KOH flakes. The vessel was closed and vacuum was increased as the temperature was increased to 140° C. The material was stirred and dried at 140° C. and about 10 mm Hg for 0.5 hrs.

The system was purged three times with nitrogen and pressurized to 25 psig. The liquid was ethoxylated with 630 gm of ethylene oxide at 140–145° C. and 65 psig. After addition was completed, the reaction mixture was digested for one hour and purged with nitrogen to remove any residual oxide. This gave a hard white waxy material at room temperature of polyoxyethylene-100 methyl glucoside.

A sample of the above PEG-100 methyl glucoside (476 gm) was placed in a flask and warmed to about 50° C. until all material melted. Oxalic acid (4.4 gm) was added in a small quantity of water. The mixture was stirred for about 0.5 hrs. and then dried under vacuum i.e., about 10 millimeters of mercury ("mm Hg") at 110° C.

Vacuum was broken with nitrogen. Then methyl oleate (101 gm) was added. The system was then purged with nitrogen. A low level of vacuum (~600 mm Hg) was developed. Using a syringe, 6.3 gm of a catalyst (tetraisopropyl titanate, Tyzor™ from Dupont) was introduced and the mixture was allowed to agitate for 10 minutes. The temperature was then increased to about 150° C.

During the next 5 hrs, the vacuum was gradually increased to 200 mm Hg. At that point, the reaction was completed and the temperature was reduced to approximately 65° C. Vacuum was broken and 50 gm of water was added to decompose catalyst. The mixture was agitated at 50° C. for 1 hr. The pH was adjusted to 6–7 with aqueous oxalic acid and then dried at high vacuum (<5 mm Hg) and 110° C. for 0.5 hrs. The product was a brown waxy solid having the following analysis:

| Parameter | Value |
|---|---|
| pH (10% in water) | 6.9 |
| Acid Value | 0.6 |
| Saponification Value | 37.0 |
| Hydroxyl Value | 14.0 |

The mixture was cooled to 80° C. as a solution of 566 gm of propylene glycol and 283 gm of water was added with stirring. This mixture was agitated for 0.5 hrs. while allowed to cool. This gave a light brown solution/blend and had a viscosity of about 2000 cP.

Example 3

Preparation of PEG-120 Methyl Glucose Trioleate-PG-Water Blend

Under a nitrogen atmosphere, a reactor was charged with 42 gm of methyl oleate and 0.8 gm of SAG-10 (anti-foaming agent from Witco Corp., Greenwich, Conn.). One thousand gm of non-neutralized Glucamate™ DOE-120 was then added. A head-space nitrogen purge was set and the mixture was heated to 175° C. Low vacuum, i.e., about 140 mmHg, was slowly applied when the temperature reached about 150° C.

Once the reaction mixture reached 175° C., the temperature was held there. After about an hour, the head-space purge was switched to a sparge. The vacuum was then slowly increased to about 5 mmHg. The mixture was reacted for an additional 5 hours.

Near the end of the cookout time, a sample was removed for methyl oleate analysis by gas chromatography. The residual methyl oleate decreased to about 0.4% (w/w) and the reaction was cooled to about 80° C., the nitrogen sparge shut off, the vacuum broken with nitrogen, and the product neutralized with an aqueous solution containing 0.6 gm of tartaric acid. The mixture was sampled for pH, color, hydroxyl number, and acid value and viscosity performance. The product, PEG-120 Methyl Glucose Trioleate, analysis showed:

| | |
|---|---|
| Performance Viscosity* | 65,000 cP |
| Hydroxyl Value | 10 |
| GH Color | 7 |

-continued

| | |
|---|---|
| pH (10% in water) | 6.5 |
| Acid Value | 0.8 |

*Performance Viscosity method as in Example #4 (Viscosity Measurement)

To prepare the blend, 1033 gm of propylene glycol (PG) was added to the warm (70–80° C.) product, PEG-120 Methyl Glucose Trioleate base prepared above. After the PG was thoroughly mixed in, heating was discontinued, and 517 gm of deionized water was added. The mixture was agitated for about 20 minutes to insure a uniform solution which was then sampled and analyzed for pH, %PG and %water. The product solution was then cooled to about 40° C. and stored. The blend had the following analysis:

| | |
|---|---|
| Water | 20% |
| Propylene glycol | 40% |
| pH (10% solids) | 6.5 |

Example 4

Viscosity Measurement

Liquid products similar to those prepared in Examples C-1, 2 and 3 were tested in a surfactant-containing liquid to determine the Viscosity Enhancement. The formulation and procedure used were as follows.

| Ingredients | wt % |
|---|---|
| Deionized Water | QS to 100 |
| Sodium Laureth Sulfate –2 (26 wt % active) | 40.00 |
| Cocamidopropyl Betaine (35 wt % active) | 11.50 |
| DMDM Hydantoin | 0.4 |
| Thickener (40 wt % polyol compound, 40 wt % propylene glycol, 20 wt % water) | 1.25 |

Procedure: Add Sodium Laureth Sulfate—2 and Cocamidopropyl Betaine to the water in order, one at a time, until completely uniform before adding the next ingredient. Once uniform add the thickener with stirring and heat to 70° C. Once the thickener is totally dissolved start cooling system to 40° C. At 40° C. add DMDM Hydantoin and continue to cool to room temperature. Record viscosity after 24 hours.

The viscosity was measured using a Brookfield RVT Viscometer with a No. 6 spindle at 10 rpm.

| Thickener Example | Viscosity, cP | Viscosity Enhancement, % |
|---|---|---|
| C-1 | 13,500 | — |
| 2 | 56,000 | 315 |
| 3 | 65,000 | 381 |

Example 5

Preparation of Body Cleansing Formula

A body cleansing formula was prepared according to the following composition and procedure.

| Ingredients | wt % |
|---|---|
| Deionized Water | QS |
| Polyquaternium-10 | 0.20 |
| Sodium Laureth Sulfate (26 wt % active) | 40.00 |
| Cocamidopropyl Betaine (35 wt % active) | 11.50 |
| Disodium Laureth Sulfosuccinate (40 wt % active) | 5.00 |
| Thickener (40 wt % polyol compound, 40 wt % propylene glycol, 20 wt % water) | 0.50 |
| DMDM Hydantoin | 0.40 |

Procedure: Add Polyquaternium-10 to room temperature deionized water with adequate agitation. When uniform heat to 70° C. and mix until fully hydrated. Once fully hydrated add the remaining ingredients up until DMDM Hydantoin, one at a time in order, waiting until for each to be dissolved before adding the next. Allow to cool to 40° C. At 40° C. add DMDM Hydantoin. Continue to cool to room temperature.

The body cleansing formula had a viscosity of 40,500 cP measured using a Brookfield RVT Viscometer with a No. 6 spindle at 10 rpm. Without the thickener, the formula had a viscosity of 3,400 cP.

Example 6

Cold Processing

A liquid product similar to that prepared in Example 2 was tested in a surfactant-containing liquid at ambient temperatures to evaluate cold processing properties. The formulation and procedure used were as follows.

| Ingredients | wt % |
|---|---|
| Deionized Water | QS to 100 |
| Sodium Laureth Sulfate –2 (26 wt % active) | 40.00 |
| Cocamidopropyl Betaine (35 wt % active) | 11.50 |
| DMDM Hydantoin | 0.4 |
| Thickener (40 wt % polyol compound, 40 wt % propylene glycol, 20 wt % water) | 1.25 |

Procedure: The Sodium Laureth Sulfate—2, Cocamidopropyl Betaine and DMDM Hydantoin were added to the water in order, one at a time, until completely uniform before adding the next ingredient. Once uniform, the thickener was added with stirring at ambient temperature and was continued until a thickening response (viscosity increase) was visually observed. The mixing was continued until completely uniform.

Although the invention has been described above with respect to specific aspects, those skilled in the art will recognize that other aspects are intended to be included within the scope of the claims which follow.

We claim:

1. A liquid composition comprising
   a) about 20 to 60 weight percent, based on the total weight of the liquid composition, of alkoxylated glucose derivatives having lipophilic substituents wherein at least 25 wt. % of the alkoxylated glucose derivatives have about 2.5 to 3.9 moles of said lipophilic substituents per mole of glucose and b) an alkylene glycol having about 2 to 5 carbon atoms per molecule.

2. The composition of claim 1 comprising an effective amount of glucose derivatives having about 2.8 to 3.6 moles of said lipophilic substituents per mole of glucose to provide a Viscosity Enhancement of at least 10%.

3. The composition of claim 2 wherein at least 50 wt. % of the glucose derivatives have about three moles of the lipophilic substituents per mole of glucose.

4. The composition of claim 1 comprising an effective amount of glucose derivatives having about three moles of said lipophilic substituents per mole of glucose to provide a Viscosity Enhancement of at least 50%.

5. The composition of claim 1 wherein less than 75 wt. % of the glucose derivatives have one, two or four or more moles of the lipophilic substituents per mole of glucose.

6. The composition of claim 1 wherein the lipophilic substituents are attached to the glucose derivatives by an ester linkage or an ether linkage.

7. The composition of claim 1 wherein the lipophilic substituents have from about 8 to about 30 carbon atoms per molecule.

8. The composition of claim 1 wherein the glucose derivatives are substituted with from about 50 to 400 moles of alkylene oxide per mole of glucose.

9. The composition of claim 8 wherein the alkylene oxide is selected from the group consisting of ethylene oxide, propylene oxide and mixtures thereof.

10. The composition of claim 1 wherein the glucose derivative is selected from the group consisting of methyl glucoside, ethyl glucoside, propyl glucoside, butyl glucoside, amyl glucoside and mixtures thereof.

11. The composition of claim 1 wherein the alkylene glycol is propylene glycol.

12. The composition of claim 1 comprising from about 10 to 30 wt. % of water, from about 30 to 50 wt. % of propylene glycol and from about 30 to 50 wt. % of the alkoxylated glucose derivatives.

* * * * *